United States Patent
Krop et al.

(10) Patent No.: US 9,504,705 B2
(45) Date of Patent: *Nov. 29, 2016

(54) HEPATITIS C VIRAL INFECTION TREATMENT USING A COMBINATION OF COMPOUNDS

(71) Applicant: ALIOS BIOPHARMA, INC., South San Francisco, CA (US)

(72) Inventors: Julie Krop, Newton, MA (US); Margaret James Koziel, Needham, MA (US); Lawrence M. Blatt, Healdsburg, CA (US); John Fry, San Francisco, CA (US); Sushmita Mukherjee Chanda, Redwood City, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/244,274

(22) Filed: Apr. 3, 2014

(65) Prior Publication Data

US 2014/0303113 A1 Oct. 9, 2014

Related U.S. Application Data

(60) Provisional application No. 61/809,283, filed on Apr. 5, 2013.

(51) Int. Cl.
| | | |
|---|---|---|
| *A01N 43/04* | (2006.01) | |
| *A61K 31/70* | (2006.01) | |
| *A01N 57/00* | (2006.01) | |
| *A61K 31/675* | (2006.01) | |
| *A61K 31/7072* | (2006.01) | |
| *A61K 31/4178* | (2006.01) | |
| *A61K 31/4196* | (2006.01) | |

(52) U.S. Cl.
CPC ....... *A61K 31/7072* (2013.01); *A61K 31/4178* (2013.01); *A61K 31/4196* (2013.01)

(58) Field of Classification Search
CPC ..................... A61K 31/7072; A61K 31/4178; A61K 31/4196; A61K 2300/00
See application file for complete search history.

(56) References Cited

U.S. PATENT DOCUMENTS

| | | | | |
|---|---|---|---|---|
| 8,772,474 B2 * | 7/2014 | Beigelman et al. | ....... | 536/26.11 |
| 8,846,896 B2 * | 9/2014 | Serebryany et al. | ....... | 536/25.33 |
| 8,871,737 B2 * | 10/2014 | Smith et al. | ..................... | 514/47 |
| 8,895,723 B2 * | 11/2014 | Serebryany et al. | ....... | 536/25.33 |
| 8,916,538 B2 * | 12/2014 | Kuldipkumar | ......... | C07H 19/06 514/43 |
| 8,980,865 B2 * | 3/2015 | Wang et al. | ..................... | 514/47 |
| 9,012,427 B2 * | 4/2015 | Blatt et al. | ..................... | 514/51 |
| 9,073,960 B2 * | 7/2015 | Beigelman | ............. | C07H 19/00 |
| 9,243,022 B2 * | 1/2016 | Beigelman | ............. | C07H 19/16 |
| 9,249,174 B2 * | 2/2016 | Beigelman | ............. | C07H 19/16 |
| 9,394,330 B2 * | 7/2016 | Kuldipkumar | ......... | C07H 19/10 |

(Continued)

FOREIGN PATENT DOCUMENTS

| | | |
|---|---|---|
| WO | WO 2010/108140 | 9/2010 |
| WO | WO 2012/088155 | 6/2012 |

(Continued)

OTHER PUBLICATIONS

International Search Report and Written Opinion dated Jun. 11, 2014 for PCT Application No. PCT/US2014/032880, filed Apr. 3, 2014.

(Continued)

*Primary Examiner* — Lawrence E Crane
(74) *Attorney, Agent, or Firm* — Knobbe, Martens, Olson & Bear, LLP

(57) ABSTRACT

Described herein is a combination that includes compound (A) of the formula

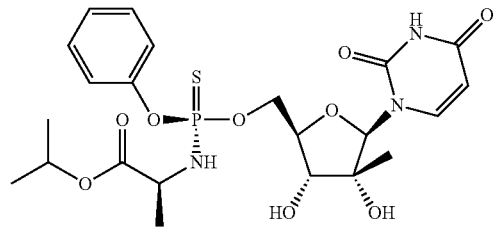

and compound (B) of the formula

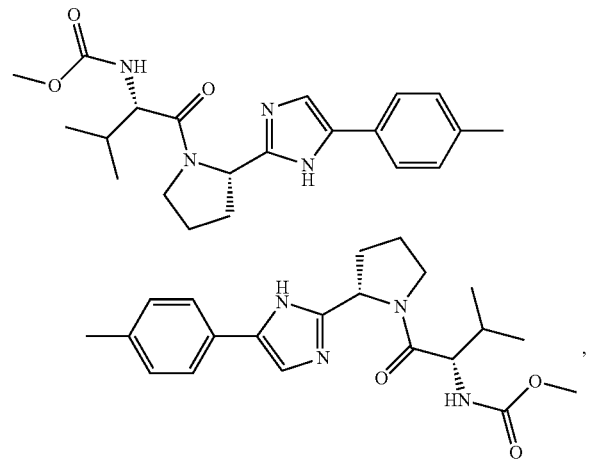

or a pharmaceutically acceptable salt(s) of the foregoing, for ameliorating and/or treating a hepatitis C viral infection.

23 Claims, 4 Drawing Sheets

(56) References Cited

U.S. PATENT DOCUMENTS

| | | |
|---|---|---|
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0165286 A1 | 6/2012 | Beigelman et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2014/0179627 A1 | 6/2014 | Beigelman et al. |
| 2014/0179910 A1 | 6/2014 | Beigelman et al. |
| 2014/0303108 A1 | 10/2014 | Beigelman et al. |
| 2014/0303113 A1 | 10/2014 | Krop et al. |
| 2015/0011497 A1 | 1/2015 | Beigelman et al. |
| 2015/0038451 A1 | 2/2015 | Smith et al. |
| 2015/0051167 A1 | 2/2015 | Wang et al. |
| 2015/0105341 A1 | 4/2015 | Beigelman et al. |
| 2015/0141363 A1 | 5/2015 | Wang et al. |
| 2015/0175647 A1 | 6/2015 | Kuldipkumar et al. |
| 2015/0183819 A1 | 7/2015 | Beigelman et al. |
| 2015/0315228 A1 | 11/2015 | Beigelman et al. |
| 2015/0366887 A1 | 12/2015 | Blatt et al. |
| 2015/0366888 A1 | 12/2015 | Blatt et al. |
| 2015/0368286 A1 | 12/2015 | Serebryany et al. |
| 2016/0016987 A1 | 1/2016 | Beigelman et al. |
| 2016/0022724 A1 | 1/2016 | Chanda et al. |
| 2016/0024136 A1 | 1/2016 | Beigelman et al. |
| 2016/0039858 A1 | 2/2016 | Beigelman et al. |
| 2016/0115190 A1 | 4/2016 | Serebryany et al. |
| 2016/0176910 A1 | 6/2016 | Wang et al. |
| 2016/0176911 A1 | 6/2016 | Beigelman et al. |

FOREIGN PATENT DOCUMENTS

| | | |
|---|---|---|
| WO | WO 2013/096679 | 6/2013 |
| WO | WO 2013/142124 | 9/2013 |
| WO | WO 2013/142157 | 9/2013 |
| WO | WO 2013/142159 | 9/2013 |
| WO | WO 2013/142525 | 9/2013 |
| WO | WO 2014/100498 | 6/2014 |
| WO | WO 2014/134251 | 9/2014 |
| WO | WO 2014/164533 | 10/2014 |
| WO | WO 2014/209983 | 12/2014 |
| WO | WO 2016/022464 | 2/2016 |

OTHER PUBLICATIONS

Casey et al., "Hepatitis C virus therapy update 2013" Curr Opin Gastroenterol. (2013) 29(3):243-249.

Sjogren et al., "The Importance of Successful Re-treatment in Refractory HCV Patients" Gastroenterol. Hepatol. (2010) 6(3 Suppl 6):1-12.

International Preliminary Report on Patentability issued Oct. 6, 2015 for PCT Application No. PCT/US2014/032880, filed Apr. 3, 2014.

* cited by examiner

Figure 1
Regime 1
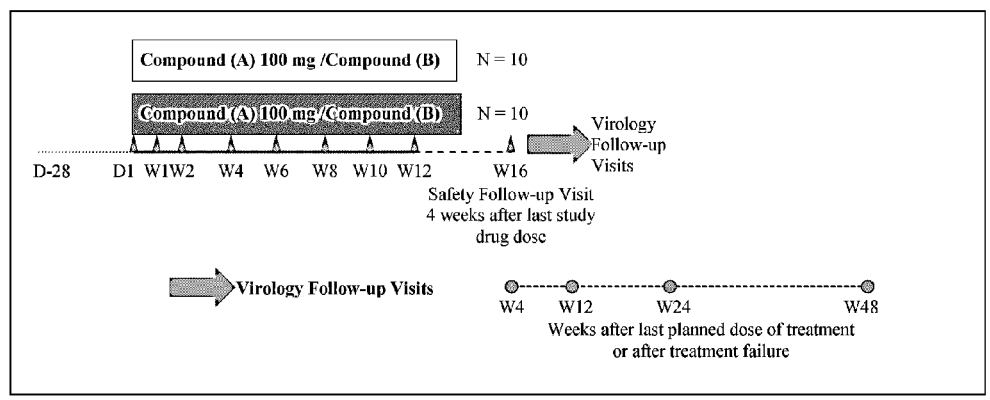
Regime 2
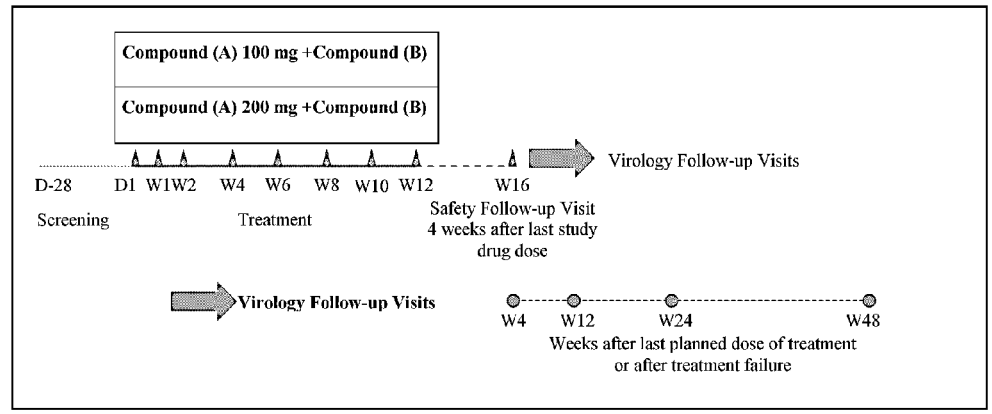

FIGURE 2: X-Ray Poweder Diffraction (XRPD) pattern/spectrum of Form J

FIGURE 3: Sold State Nuclear Magnetic Resonance (ssNMR) Spectrum of Form J

HEPATITIS C VIRAL INFECTION TREATMENT USING A COMBINATION OF COMPOUNDS

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57.

BACKGROUND

Field

The present application relates to the fields of chemistry, biochemistry and medicine. More particularly, disclosed herein are a method of ameliorating and/or treating hepatitis C virus (HCV) infection using a combination of agents.

Description

Hepatitis C virus (HCV) is a positive-single stranded RNA virus belonging to the Flaviviridae family. HCV can be transmitted via the blood. According to the Center for Disease Control and Prevention, over 3 million people in the United States are infected.

SUMMARY

Some embodiments described herein generally relate to a method for ameliorating or treating a hepatitis C viral infection that can include administering to a subject suffering from the hepatitis C viral infection an effective amount of a combination of compound (A) and compound (B), or a pharmaceutically acceptable salt of the foregoing; wherein: compound (A) is

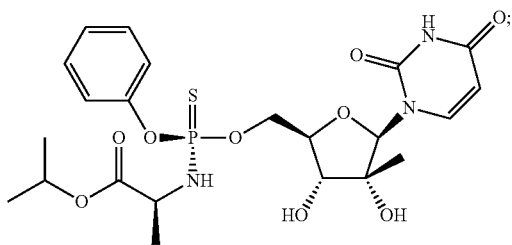 [SMILES: CC(C)OC(=O)[C@H](C)N[P@](=S)(OC[C@H]1O[C@@H](n2ccc(=O)[nH]c2=O)[C@](C)(O)[C@@H]1O)Oc1ccccc1]

compound (B) is

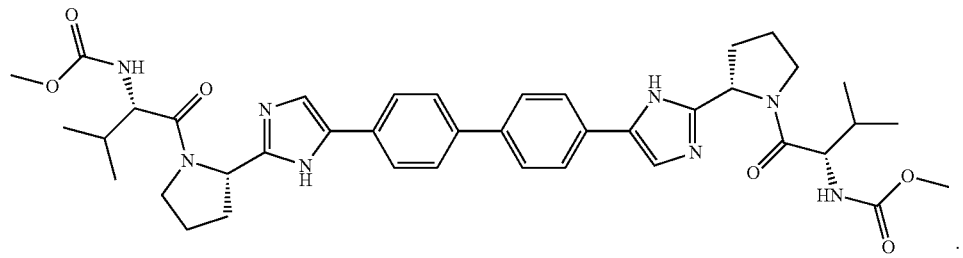

(daclatasvir)

Other embodiments described herein generally relate to a method for ameliorating or treating a hepatitis C viral infection that can include contacting a cell infected with a hepatitis C virus with an effective amount of a combination of compound (A) and compound (B), or a pharmaceutically acceptable salt of the foregoing.

Still other embodiments described herein generally relate to a method for inhibiting the replication of a hepatitis C virus that can include contacting a cell infected with the hepatitis C virus with an effective amount of a combination of compound (A) and compound (B), or a pharmaceutically acceptable salt of the foregoing.

BRIEF DESCRIPTION OF THE DRAWINGS

FIG. 1 shows two exemplary treatment regimes.

DETAILED DESCRIPTION

Figure 2:
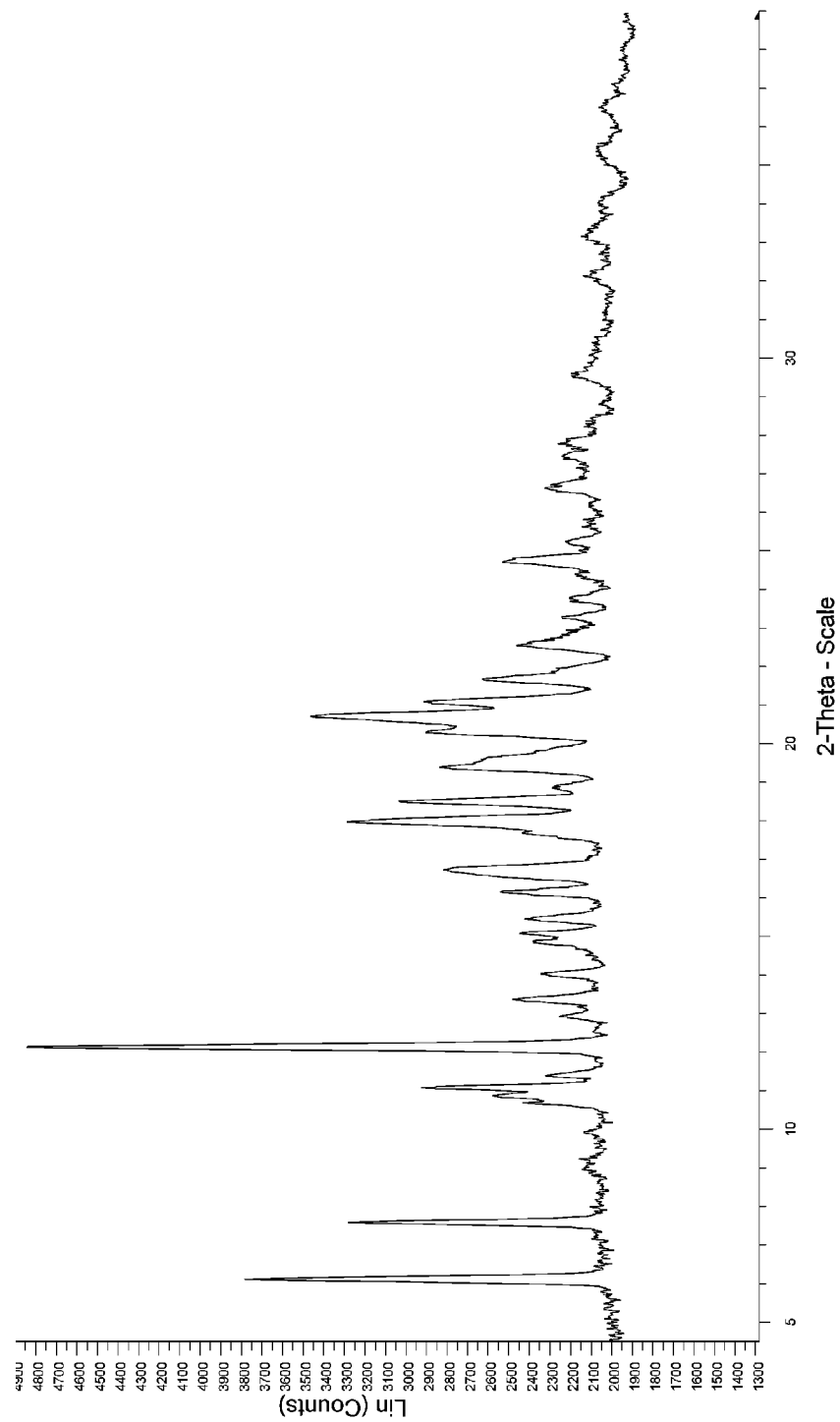
FIG. 2 shows an XRPD pattern of Form J.

Some embodiments described herein relate to a method of ameliorating and/or treating a HCV infection in a subject suffering from the HCV infection that can include administering to the subject an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for ameliorating and/or treating a HCV infection in a subject suffering from the HCV infection that can include administering to the subject an effective amount of said combination of compounds. Still other embodiments described herein relate to a combination of compound (A) and compound (B), or a pharmaceutically acceptable salt of the foregoing, that can be used for ameliorating and/or treating a HCV infection in a subject suffering from the HCV infection that can include administering to the subject an effective amount of said combination of compounds.

Some embodiments disclosed herein relate to a method of ameliorating and/or treating a HCV viral infection that can include contacting a cell infected with the virus with an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for ameliorating and/or treating a HCV viral infection that can include contacting a cell infected with the virus with an effective amount of said combination of compounds. Still other embodiments described herein relate to a combination of compound (A)

and compound (B), or a pharmaceutically acceptable salt of the foregoing, that can be used for ameliorating and/or treating a HCV viral infection by contacting a cell infected with the virus with an effective amount of said combination of compounds.

Some embodiments disclosed herein relate to a method of inhibiting replication of a HCV virus that can include contacting a cell infected with the virus with an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for inhibiting replication of a HCV virus that can include contacting a cell infected with the virus with an effective amount of said combination of compounds. Still other embodiments described herein relate to a combination of compound (A) and compound (B), or a pharmaceutically acceptable salt of the foregoing, that can be used for inhibiting replication of a HCV virus by contacting a cell infected with the virus with an effective amount of said combination of compounds.

Some embodiments described herein relate to a method of inhibiting a HCV polymerase can include contacting a cell infected with HCV with an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for inhibiting a HCV polymerase that can include contacting a cell infected with HCV with an effective amount of said combination of compounds. Still other embodiments described herein relate to a combination of compound (A) and compound (B), or a pharmaceutically acceptable salt of the foregoing, that can be used for inhibiting a HCV polymerase that can include contacting a cell infected with HCV with an effective amount of said combination of compounds.

Some embodiments described herein relate to a method of ameliorating and/or treating a condition selected from liver fibrosis, liver cirrhosis, and liver cancer in a subject suffering from one or more of the aforementioned liver conditions, wherein one or more of the aforementioned liver conditions is caused by a HCV infection, that can include administering an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for ameliorating and/or treating a condition selected from liver fibrosis, liver cirrhosis, and liver cancer in a subject suffering from one or more of the aforementioned liver conditions, wherein one or more of the aforementioned liver conditions is due to a HCV infection, that can include administering an effective amount of said combination of compounds. Still other embodiments described herein relate to a combination of compound (A) and compound (B), or a pharmaceutically acceptable salt of the foregoing, that can be used for ameliorating and/or treating a condition selected from liver fibrosis, liver cirrhosis, and liver cancer in a subject suffering from one or more of the aforementioned liver conditions, wherein one or more of the aforementioned liver conditions is from a HCV infection, that can include administering an effective amount of said combination of compounds.

Some embodiments described herein relate to a method of increasing liver function in a subject having a HCV infection that can include administering to the subject an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for increasing liver function in a subject having a HCV infection that can include administering to the subject an effective amount of said combination of compounds. Still other embodiments described herein relate to a combination of compound (A) and compound (B), or a pharmaceutically acceptable salt of the foregoing, that can be used for increasing liver function in a subject having a HCV infection that can include administering to the subject an effective amount of said combination of compounds.

Also contemplated is a method for reducing or eliminating further virus-caused liver damage in a subject having a HCV infection by administering an effective amount of a combination of compound (A) and compound (B), or a pharmaceutically acceptable salt of the foregoing. Other embodiments described herein relate to using a combination of compound (A) and compound (B), or a pharmaceutically acceptable salt of the foregoing, in the manufacture of a medicament for reducing or eliminating further virus-caused liver damage in a subject having a HCV infection by administering an effective amount of said combination of compounds. Still other embodiments described herein relate to a combination of compound (A) and compound (B), or a pharmaceutically acceptable salt of the foregoing, that can be used for reducing or eliminating further virus-caused liver damage in a subject having a HCV infection by administering an effective amount of said combination of compounds.

In some embodiments, the groups attached to the thiophosphate of compound (A) can be removed by simple hydrolysis. Inside the cell, the thio-monophosphate thus released may then be metabolized by cellular enzymes to the alpha-thiodiphosphate or the active alpha-thiotriphosphate. Some embodiments described herein relate to a method for ameliorating and/or treating a HCV viral infection in a subject suffering from the viral infection that can include contacting a cell infected with the virus with an effective amount of a combination of compound (B) and the alpha-thiotriphosphate formed from compound (A), or a pharmaceutically acceptable salt of the foregoing. Other embodiments described herein relate to using an effective amount of a combination of compound (B) and the alpha-thiotriphosphate formed from compound (A), or a pharmaceutically acceptable salt of the foregoing, in the manufacture of a medicament for ameliorating and/or treating a HCV viral infection that can include contacting a cell infected with HCV with an effective amount of said combination. Still other embodiments described herein relate to a combination of compound (B) and the alpha-thiotriphosphate formed from compound (A), or a pharmaceutically acceptable salt of the foregoing, that can be used for ameliorating and/or treating a HCV viral infection that can include contacting a cell infected with HCV with an effective amount of said combination.

In some embodiments, a method and/or use described herein (for example, the methods and/or uses provided in paragraphs [0004]-[0018]) can further include compound (C), or a pharmaceutically acceptable salt thereof, wherein compound (C) is

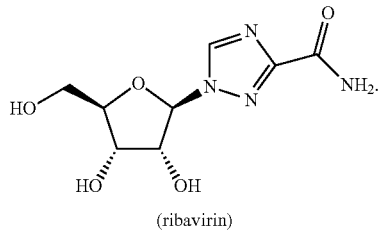 [SMILES: NC(=O)c1ncn([C@@H]2O[C@H](CO)[C@@H](O)[C@H]2O)n1]

(ribavirin)

The dosages of compounds (A), (B) and (C), or a pharmaceutical acceptable salt of the foregoing, can vary. In some embodiments, compound (A) can be dosed in an amount in the range of about 50 mg to about 300 mg. In some embodiments, compound (A) can be dosed in an amount in the range of about 100 mg to about 200 mg. In some embodiments, compound (A) can be dosed in an amount of about 100 mg. In other embodiments, compound (A) can be dosed in an amount of about 200 mg. Compound (A) can be provided at various times. For example, in some embodiments, compound (A) can be provided once daily. Multiple routes of administration exist for providing compound (A). In some embodiments, compound (A) can be administered orally.

In some embodiments, compound (A) can be Form J of compound (A).

In some embodiments, Form J can be characterized by an X-ray powder diffraction pattern of FIG. 1. In some embodiments, Form J can be characterized by one or more XRPD peaks selected from the table below.

| No. | 2-Theta ° | Intensity % |
|---|---|---|
| 1 | 6.1* | 69.2 |
| 2 | 7.5* | 54.4 |
| 3 | 9.0 | 21.2 |
| 4 | 9.9 | 21.2 |
| 5 | 10.8 | 34.0 |
| 6 | 11.1 | 44.2 |
| 7 | 11.4 | 26.5 |
| 8 | 12.1* | 100.0 |
| 9 | 12.9 | 24.6 |
| 10 | 13.3* | 31.2 |
| 11 | 14.0* | 27.2 |
| 12 | 14.8 | 28.3 |
| 13 | 15.1 | 30.2 |
| 14 | 15.4 | 29.5 |
| 15 | 16.1 | 33.0 |
| 16 | 16.7 | 41.0 |
| 17 | 17.6 | 29.8 |
| 18 | 18.0 | 54.6 |
| 19 | 18.5* | 47.3 |
| 20 | 18.9 | 25.6 |
| 21 | 19.4 | 41.6 |
| 22 | 19.6 | 35.8 |
| 23 | 20.3 | 43.5 |
| 24 | 20.7 | 59.8 |
| 25 | 21.1 | 43.8 |
| 26 | 21.7 | 35.5 |
| 27 | 22.6** | 30.1 |
| 28 | 22.3 | 24.3 |
| 29 | 23.8 | 23.1 |
| 30 | 24.7 | 32.7 |
| 31 | 25.2 | 23.7 |
| 32 | 25.7 | 20.8 |
| 33 | 26.6 | 26.7 |
| 34 | 27.5 | 24.3 |
| 35 | 27.8 | 23.6 |
| 36 | 28.3 | 20.7 |
| 37 | 29.6 | 22.9 |
| 38 | 32.2 | 20.3 |
| 39 | 33.2** | 21.5 |
| 40 | 34.0** | 19.2 |
| 41 | 35.3** | 19.3 |
| 42 | 35.4 | 19.4 |
| 43 | 36.5 | 19.0 |

Peaks with an asterisk (*) are major peaks
Peaks with a double asterisk (**) are secondary peaks In some embodiments, Form J can be characterized by a $^{13}$C NMR solid state spectrum of FIG. 2. In some embodiments, Form J can be characterized by one or more peaks in a $^{13}$C NMR solid state spectrum selected from the table below.

| Peak | v(F1) [ppm] | Intensity [rel] |
|---|---|---|
| 1 | 175.6* | 26.8 |
| 2 | 172.6 | 39.76 |
| 3 | 165.8 | 13.72 |
| 4 | 162.9 | 22.43 |
| 5 | 162.5 | 16.16 |
| 6 | 153.0 | 15.82 |
| 7 | 152.8 | 15.88 |
| 8 | 151.5 | 29.40 |
| 9 | 151.1 | 11.45 |
| 10 | 150.7 | 36.85 |
| 11 | 150.1 | 21.71 |
| 12 | 141.4* | 19.34 |
| 13 | 140.1 | 11.81 |
| 14 | 131.1 | 29.77 |
| 15 | 129.7 | 35.60 |
| 16 | 129.5 | 26.33 |
| 17 | 127.8* | 25.20 |
| 18 | 127.1 | 17.58 |
| 19 | 126.3 | 27.54 |
| 20 | 123.8 | 29.09 |
| 21 | 123.4* | 32.43 |
| 22 | 122.8 | 26.21 |
| 23 | 103.1* | 37.64 |
| 24 | 101.3 | 27.86 |
| 25 | 93.8 | 22.55 |
| 26 | 93.3 | 16.53 |
| 27 | 91.7 | 18.80 |
| 28 | 83.5* | 35.20 |
| 29 | 81.1* | 35.52 |
| 30 | 80.7 | 100.00 |
| 31 | 79.8 | 28.76 |
| 32 | 78.6 | 42.08 |
| 33 | 74.4 | 37.67 |
| 34 | 73.4 | 41.04 |
| 35 | 73.1 | 28.84 |
| 36 | 72.3 | 39.74 |
| 37 | 70.1 | 57.8 |
| 38 | 63.7 | 44.0 |
| 39 | 62.2* | 33.4 |
| 40 | 53.1 | 21.6 |
| 41 | 52.5 | 16.9 |
| 42 | 50.8 | 15.9 |
| 43 | 25.6* | 36.7 |
| 44 | 23.7 | 60.6 |
| 45 | 23.0 | 34.4 |
| 46 | 22.5 | 64.4 |
| 47 | 22.1 | 46.4 |
| 48 | 21.7 | 36.1 |
| 49 | 19.6* | 34.5 |
| 50 | 18.8 | 34.8 |
| 51 | 18.4 | 29.1 |

Peaks with an asterisk (*) are major peaks

Figure 3:
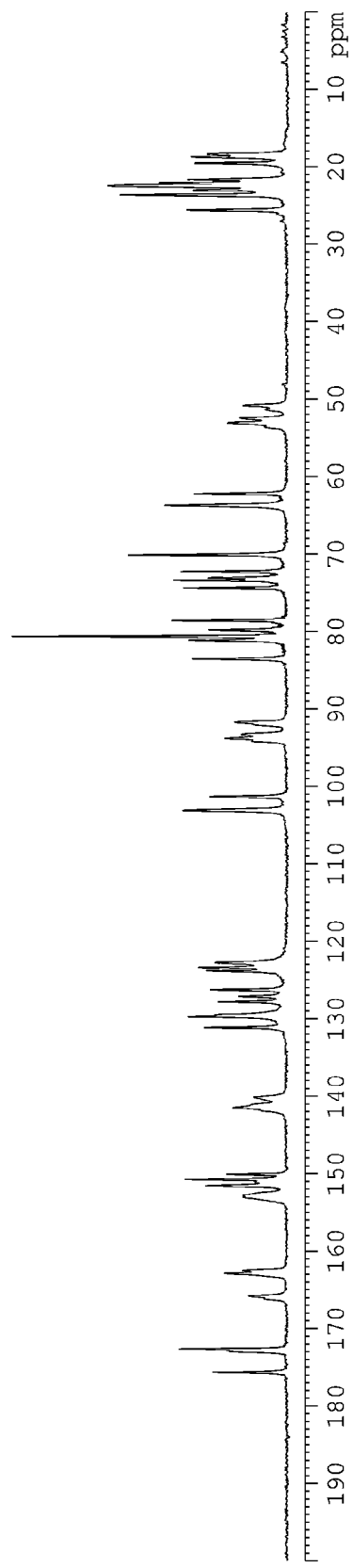
FIG. 3 shows a $^{13}C$ solid state NMR spectrum of Form J.
Figure 4:
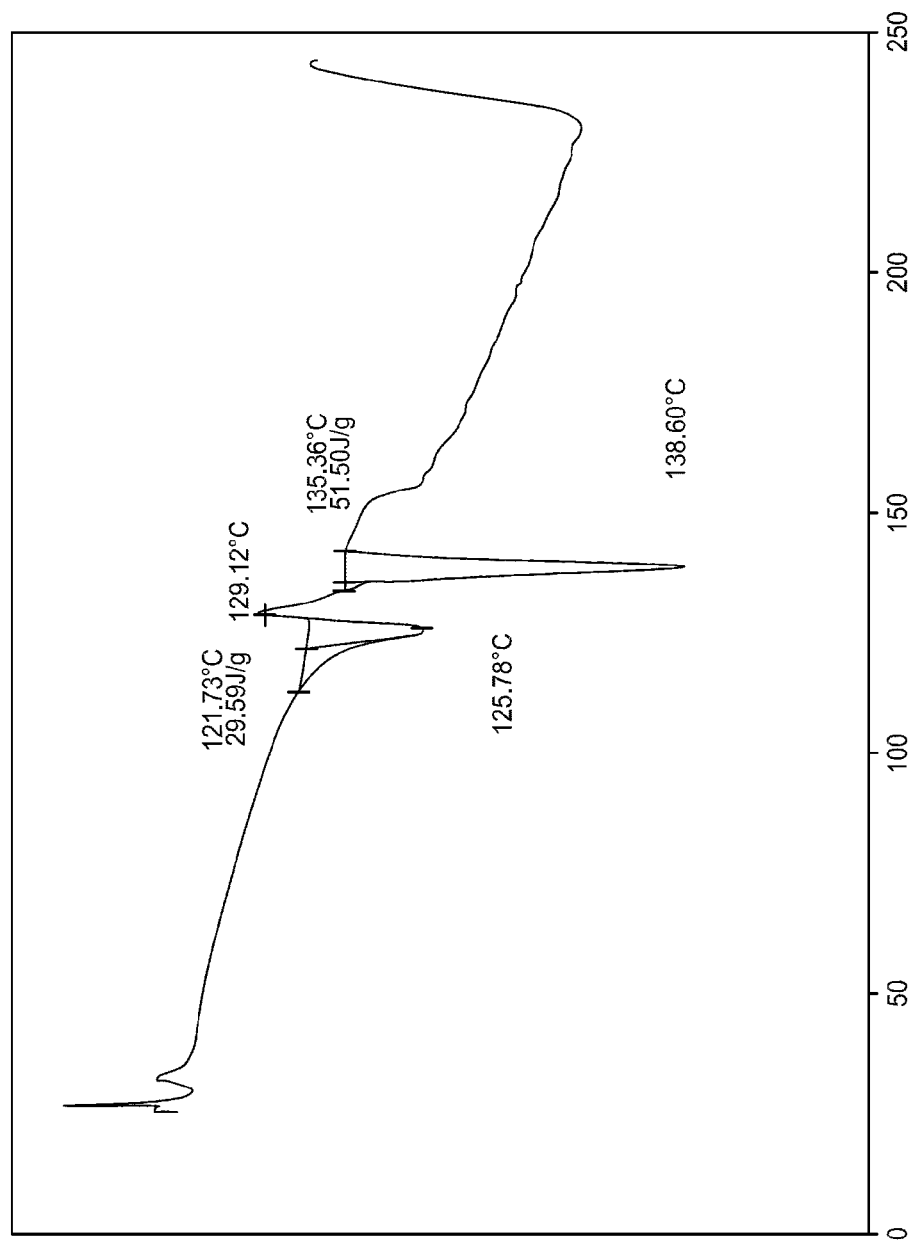
FIG. 4 shows a DSC thermogram of Form J.

In some embodiments, Form J can be characterized by a DSC thermogram as shown in FIG. 3. In some embodiments, Form J can be characterized by a DSC thermogram showing a first endotherm in the range of about 121° C. to about 127° C. (for example, at about 126° C.), an exotherm in the range of about 127° C. to about 132° C. (for example, at about 129° C.), and a second endotherm in the range of about 135° C. to about 142° C. (for example, at about 138° C.).

In some embodiments, compound (B) can be dosed in an amount in the range of about 40 mg to about 80 mg. In some embodiments, compound (B) can be dosed in an amount in the range of about 50 mg to about 70 mg. In some embodiments, compound (B) can be dosed in an amount of about 60 mg. As with compound (A), the timing and route of administration of compound (B) can vary. In some embodiments, compound (B) can be dosed once daily. In some embodiments, compound (B) can be provided orally.

In some embodiments, compound (C) can be dosed twice daily. In some embodiments, the total daily dose of compound (C) can be in an amount in the range of about 800 mg to about 1400 mg. When compound (C) is provided twice daily, the amount of the total dosage of the two dosages of compound (C) can be in the range of about 800 mg to about 1400 mg. In some embodiments, the total daily dose of compound (C) can be in an amount in the range of about 900 mg to about 1300 mg. In some embodiments, the total daily dose of compound (C) can be in an amount in the range of about 1000 mg to about 1200 mg. The total daily dose or compound (C), or a pharmaceutically acceptable salt thereof, can be split equally between the two daily doses or unequally between the two daily doses.

Various lengths of the treatment can exist for a combination described herein (for example, compound (A) compound (B) and optionally compound (C), or a pharmaceutically acceptable salt of the foregoing). In some embodiments, a combination of compound (A), compound (B) and optionally compound (C), or a pharmaceutically acceptable salt of the foregoing, can be provided for less than 24 weeks. In some embodiments, a combination of compound (A), compound (B) and optionally compound (C), or a pharmaceutically acceptable salt of the foregoing, can be provided for less than 48 weeks. In some embodiments, a combination of compound (A), compound (B) and optionally compound (C), or a pharmaceutically acceptable salt of the foregoing, can be provided for about 12 weeks. In some embodiments, a combination of compound (A), compound (B) and optionally compound (C), or a pharmaceutically acceptable salt of the foregoing, can be provided in the range of 12 weeks to 24 weeks.

Any orally acceptable dosage form including, but not limited to, capsules, tablets, pills, powders, granules, emulsions, microemulsions, suspensions (e.g., aqueous suspensions), syrups, elixirs, or solutions can be used to provide compound (A) and compound (B), or a pharmaceutically acceptable salt of the foregoing. Liquid dosage forms for oral administration include, but are not limited to, pharmaceutically acceptable emulsions, microemulsions, solutions, suspensions, syrups and elixirs. Solid dosage forms for oral administration include capsules (for example, soft and hard-filled gelatin capsules), tablets, pills, powders, and granules. The oral dosage forms can be prepared using methods known to those skilled in the art and may contain additional materials such as pharmaceutically acceptable excipient(s) or carrier(s).

Combination of pegylated interferon plus ribavirin is the current standard of care for a HCV infection. This treatment does not provide sustained viral response (SVR) in a majority of subjects infected with the most prevalent genotype (1a and 1b). Furthermore, significant side effects prevent compliance to the current regimen and may require dose reduction or discontinuation in some subjects.

The standard of care (SOC) for the treatment of HCV infection comprises a 48-week administration of a combination of pegylated interferon-α (subcutaneous weekly injection) and ribavirin (oral, twice daily). The SOC therapy is poorly tolerated and ultimately successful in less than half of the treated subject population. Accordingly, there is a need for the continued development of treatment regimes.

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, a combination of compound (A), compound (B) and optionally compound (C), or a pharmaceutically acceptable salt of the foregoing, can be effective to treat at least one genotype of HCV. In some embodiments, a combination of compound (A), compound (B) and optionally compound (C), or a pharmaceutically acceptable salt of the foregoing, can be effective to treat all 11 genotypes of HCV. In some embodiments, a combination of compound (A), compound (B) and optionally compound (C), or a pharmaceutically acceptable salt of the foregoing, can be effective to treat 3 or more, 5 or more, 7 or more of 9 more genotypes of HCV. In some embodiments, a combination of compound (A), compound (B) and optionally compound (C), or a pharmaceutically acceptable salt of the foregoing, can be more effective against a larger number of HCV genotypes than the standard of care. In some embodiments, a combination of compound (A), compound (B) and optionally compound (C), or a pharmaceutically acceptable salt of the foregoing, can be more effective against a particular HCV genotype than the standard of care (such as genotype 1, 2, 3, 4, 5 and/or 6). In some embodiments, a combination of compound (A), compound (B) and optionally compound (C), or a pharmaceutically acceptable salt of the foregoing, can be effective to ameliorate and/or treat genotype selected from 1, 2, 3, 4, 5 and 6. In some embodiments, a combination of compound (A), compound (B) and optionally compound (C), or a pharmaceutically acceptable salt of the foregoing, can be effective to ameliorate and/or treat genotype 1. In other embodiments, a combination of compound (A), compound (B) and optionally compound (C), or a pharmaceutically acceptable salt of the foregoing, can be effective to ameliorate and/or treat genotype 2. In still other embodiments, a combination of compound (A), compound (B) and optionally compound (C), or a pharmaceutically acceptable salt of the foregoing, can be effective to ameliorate and/or treat genotype 3. In yet still other embodiments, a combination of compound (A), compound (B) and optionally compound (C), or a pharmaceutically acceptable salt of the foregoing, can be effective to ameliorate and/or treat genotype 4. In some embodiments, a combination of compound (A), compound (B) and optionally compound (C), or a pharmaceutically acceptable salt of the foregoing, can be effective to ameliorate and/or treat genotype 5. In other embodiments, a combination of compound (A), compound (B) and optionally compound (C), or a pharmaceutically acceptable salt of the foregoing, can be effective to ameliorate and/or treat genotype 6. In still other embodiments, a combination of compound (A), compound (B) and optionally compound (C), or a pharmaceutically acceptable salt of the foregoing, can be effective to ameliorate and/or treat genotype 1a.

Various indicators for determining the effectiveness of a method for treating a HCV infection are known to those skilled in the art. Example of suitable indicators include, but are not limited to, a reduction in viral load, a reduction in viral replication, a reduction in time to seroconversion (virus undetectable in subject serum), an increase in the rate of sustained viral response to therapy, a reduction of morbidity or mortality in clinical outcomes, a reduction in the rate of liver function decrease, stasis in liver function, improvement in liver function, reduction in one or more markers of liver dysfunction, including alanine transaminase, aspartate transaminase, total bilirubin, conjugated bilirubin, gamma glutamyl transpeptidase, and/or other indicator of disease response. Similarly, successful therapy with a combination therapy described herein (e.g., a combination of compound (A), compound (B) and optionally compound (C), or a pharmaceutically acceptable salt of the foregoing) can reduce the incidence of liver cancer in HCV subjects and/or the severity of liver cirrhosis in HCV subjects In some embodiments, a combination of compound (A), compound (B) and optionally compound (C), or a pharmaceutically acceptable salt of the foregoing, can be effective to reduce viral titers to undetectable levels, to about 100 to about 500, to about 50 to about 100, to about 10 to about 50, or to about 15 to about 25 international units/mL serum. In some embodiments, a combination of compound (A), compound (B) and optionally compound (C), or a pharmaceutically acceptable salt of the foregoing, can be effective to reduce the viral load compared to the viral load before administration of a combination of compound (A), compound (B) and optionally compound (C), or a pharmaceutically acceptable salt of the foregoing. For example, wherein the viral load is measured before administration of a combination of compound (A), compound (B) and optionally compound (C), or a pharmaceutically acceptable salt of the foregoing, and again after completion of the treatment regime with a combination of compound (A), compound (B) and optionally compound (C), or a pharmaceutically acceptable salt of the foregoing. In some embodiments, an amount of a combination of compound (A), compound (B) and optionally compound (C), or a pharmaceutically acceptable salt of the foregoing, can be an amount that is effective to reduce viral load to lower than about 25 international units/mL of serum. In some embodiments, an amount of a combination of compound (A), compound (B) and optionally compound (C), or a pharmaceutically acceptable salt of the foregoing, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of a combination of compound (A), compound (B) and optionally compound (C), or a pharmaceutically acceptable salt of the foregoing. For example, the viral load can be measured before administration of a combination of compound (A), compound (B) and optionally compound (C), or a pharmaceutically acceptable salt of the foregoing, and again after completion of the treatment regime with a combination of compound (A), compound (B) and optionally compound (C), or a pharmaceutically acceptable salt of the foregoing. In some embodiments, including those of this paragraph, a reduction of viral load can be observed when comparing the viral load measured prior to the start of treatment with a combination described herein (for example, a combination of compound (A), compound (B) and optionally compound (C), or a pharmaceutically acceptable salt of the foregoing) and then 24 weeks after completion of treatment. In other embodiments, including those of this paragraph, a reduction of viral load can be observed when comparing the viral load measured prior to the start of treatment with a combination described herein (for example, a combination of compound (A), compound (B) and optionally compound (C), or a pharmaceutically acceptable salt of the foregoing) and then 4 weeks after completion of treatment. In still other embodiments, including those of this paragraph, a reduction of viral load can be observed when comparing the viral load measured prior to the start of treatment with a combination described herein (for example, a combination of compound (A), compound (B) and optionally compound (C), or a pharmaceutically acceptable salt of the foregoing) and then 4 weeks after completion of treatment.

In some embodiments, a combination of compound (A), compound (B) and optionally compound (C), or a pharmaceutically acceptable salt of the foregoing, can result in at least a 1, 2, 3, 4, 5, 10, 15, 20, 25, 50, 75, 100-fold or more reduction in the replication of HCV relative to pre-treatment levels in a subject, as determined after completion of the treatment regime. In some embodiments, a combination of compound (A), compound (B) and optionally compound (C), or a pharmaceutically acceptable salt of the foregoing, can result in a reduction of the replication of HCV relative to pre-treatment levels in the range of about 2 to about 5 fold, about 10 to about 20 fold, about 15 to about 40 fold, or about 50 to about 100 fold. In some embodiments, including those of this paragraph, a reduction of HCV replication can be observed when comparing the level of HCV measured prior to the start of treatment with a combination described herein (for example, a combination of compound (A), compound (B) and optionally compound (C), or a pharmaceutically acceptable salt of the foregoing) and then 24 weeks after completion of treatment. In other embodiments, including those of this paragraph, a reduction of HCV replication can be observed when comparing the level of HCV measured prior to the start of treatment with a combination described herein (for example, a combination of compound (A), compound (B) and optionally compound (C), or a pharmaceutically acceptable salt of the foregoing) and then 4 weeks after completion of treatment. In still other embodiments, including those of this paragraph, a reduction of HCV replication can be observed when comparing the level of HCV measured prior to the start of treatment with a combination described herein (for example, a combination of compound (A), compound (B) and optionally compound (C), or a pharmaceutically acceptable salt of the foregoing) and then 12 weeks after completion of treatment.

In some embodiments, a combination of compound (A), compound (B) and optionally compound (C), or a pharmaceutically acceptable salt of the foregoing, can result in a reduction of HCV replication in the range of 1 to 1.5 log, 1.5 log to 2 log, 2 log to 2.5 log, 2.5 to 3 log, 3 log to 3.5 log or 3.5 to 4 log more reduction of HCV replication compared to the reduction of HCV replication achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, a combination of compound (A), compound (B) and optionally compound (C), or a pharmaceutically acceptable salt of the foregoing, can be effective to achieve a sustained viral response, for example, non-detectable or substantially non-detectable HCV RNA (e.g., less than about 500, less than about 400, less than about 200, less than about 100, or less than 25 international units per milliliter of serum) is found in the subject's serum, for a period of at least about one month, at least about two months, at least about three months, at least about four months, at least about five months, or at least about six months following cessation of therapy. In some embodiments, a combination of compound (A), compound (B) and optionally compound (C), or a pharmaceutically acceptable salt of the foregoing, can be effective to achieve a sustained viral response, for example, non-detectable or substantially non-detectable HCV RNA (e.g., less than about 500, less than about 400, less than about 200, less than about 100, or 25 international units per milliliter of serum) is found in the subject's serum, for a period of at least 4 weeks following cessation of therapy. In some embodiments, a combination of compound (A), compound (B) and optionally compound (C), or a pharmaceutically acceptable salt of the foregoing, can be effective to achieve a sustained viral response for a period of at least 12 weeks following cessation of therapy.

In some embodiments, a combination of compound (A), compound (B) and optionally compound (C), or a pharmaceutically acceptable salt of the foregoing, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), asparatate aminotransferacse (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a combination of compound (A), compound (B) and optionally compound (C), or a pharmaceutically acceptable salt of the foregoing, is an amount effective to reduce ALT, AST, ALP, GGT and/or TBIL levels to within what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a combination of compound (A), compound (B) and optionally compound (C), or a pharmaceutically acceptable salt of the foregoing, can be administered to a naïve subject suffering from HCV. In other embodiments, a combination of compound (A), compound (B) and optionally compound (C), or a pharmaceutically acceptable salt of the foregoing, can be administered to a treatment failure subject suffering from HCV. In some embodiments, a combination of compound (A), compound (B) and optionally compound (C), or a pharmaceutically acceptable salt of the foregoing, can be administered to a non-responder subject suffering from HCV. In some embodiments, a combination of compound (A), compound (B) and optionally compound (C), or a pharmaceutically acceptable salt of the foregoing, can be administered to a relapsed subject suffering from HCV. In some embodiments of this paragraph, the subject can have cirrhosis of the liver.

After a period of time, infectious agents can develop resistance to one or more therapeutic compounds. The term "resistance" as used herein refers to a viral strain displaying a delayed, lessened and/or null response to a therapeutic compound(s). For example, after treatment with an antiviral agent, the viral load of a subject infected with a resistant virus may be reduced to a lesser degree compared to the amount in viral load reduction exhibited by a subject infected with a non-resistant strain. In some embodiments, a combination of compound (A), compound (B) and optionally compound (C), or a pharmaceutically acceptable salt of the foregoing, can be administered to a subject infected with a HCV strain that is resistant to one or more different anti-HCV agents. In some embodiments, development of resistant HCV strains is delayed when subjects are treated with a combination of compound (A), compound (B) and optionally compound (C), or a pharmaceutically acceptable salt of the foregoing, compared to the development of HCV strains resistant to other HCV drugs. In some embodiments, including those of this paragraph, the resistance can be resistance to ribavirin, peginterferon alfa-2a (PEGASYS®), peginterferon alfa-2b (PEGATRON®), boceprevir and/or telaprevir.

In some embodiments, an effective amount of a combination of compound (A), compound (B) and optionally compound (C), or a pharmaceutically acceptable salt of the foregoing, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of the current SOC therapy. In some embodiments, a combination of compound (A), compound (B) and optionally compound (C), or a pharmaceutically acceptable salt of the foregoing, can be provided to a subject that is hypersensitive to interferon.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a combination of compound (A), compound (B) and optionally compound (C), or a pharmaceutically acceptable salt of the foregoing, can be administered to a subject experiencing viral load rebound, or can prevent such viral load rebound when used to treat the subject.

The standard of care for treating HCV has been associated with several side effects (adverse events). In some embodiments, a combination of compound (A), compound (B) and optionally compound (C), or a pharmaceutically acceptable salt of the foregoing, can decrease the number and/or severity of one or more side effects that can be observed in HCV subjects being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a combination of compound (A), compound (B) and optionally compound (C), or a pharmaceutically acceptable salt of the foregoing, can be provided to a subject that discontinued a HCV therapy because of one or more adverse effects or side effects associated with one or more other HCV agents (for example, ribavirin, peginterferon alfa-2a (PEGASYS®), peginterferon alfa-2b (PEGATRON®), boceprevir and/or telaprevir).

Table A provides some embodiments of a combination of compound (A), compound (B) and optionally compound (C), or a pharmaceutically acceptable salt of the foregoing, compared to the standard of care. Examples include the following: in some embodiments, a combination as described herein of a combination of compound (A), compound (B) and optionally compound (C), or a pharmaceutically acceptable salt of the foregoing, can result in a percentage of non-responders that is 10% less than the percentage of non-responders resulting from the standard of care; in some embodiments, a combination of compound (A), compound (B) and optionally compound (C), or a pharmaceutically acceptable salt of the foregoing, can result in a number of side effects that is in the range of about 10% to about 30% less than compared to the number of side effects experienced by a subject receiving the standard of care; and in some embodiments, a combination of compound (A), compound (B) and optionally compound (C), or a pharmaceutically acceptable salt of the foregoing, can result in a severity of a side effect (such as one of those described herein) that is 25% less than compared to the severity of the same side effect experienced by a subject receiving the standard of care. Methods of quantifying the severity of a side effect are known to those skilled in the art.

TABLE A

| Percentage of non-responders | Percentage of relapsers | Percentage of resistance | Percentage of viral load rebound | Number of side effects | Severity of side effects |
| --- | --- | --- | --- | --- | --- |
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The term "effective amount" is used to indicate an amount of an active compound, or pharmaceutical agent, or combination of compounds or agents, that elicits the biological or medicinal response indicated. For example, an effective amount of compound can be the amount needed to prevent, alleviate or ameliorate a symptom of disease or prolong the survival of the subject being treated. For a combination, it is not necessary that each component be individually present in an effective amount; rather, all that is required is that there be an effective amount of a combination described herein. Preferably, each of the recited active components contributes to that collective effectiveness. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual subject. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Compound (A), compound (B) and compound (C) can be contained in a single unit dosage form, in two unit dosage forms, or in three unit dosage forms.

In some embodiments, a single unit dosage form can be include compound (A) and compound (B). In other embodiments, one unit dosage form can include compound (A) and another unit dosage form can include compound (B). If compound (C) is part of the combination therapy, compound (C) can be present with compound (A) and/or compound (B), or compound (C) can be in a separate unit dosage form.

The order of administration of a combination of a combination of compound (A), compound (B) and optionally compound (C), or a pharmaceutically acceptable salt of the foregoing, can vary. In some embodiments, compound (A), or a pharmaceutically acceptable salt thereof, can be administered prior to all compounds of the combination therapy. In other embodiments, compound (A), or a pharmaceutically acceptable salt thereof, can be administered prior to at least one compound of the combination therapy. In still other embodiments, compound (A), or a pharmaceutically acceptable salt thereof, can be administered concomitantly with one or more compound(s) of the combination therapy. In yet still other embodiments, compound (A), or a pharmaceutically acceptable salt thereof, can be administered subsequent to the administration of at least one compound of the combination therapy. In some embodiments, compound (A), or a pharmaceutically acceptable salt thereof, can be administered subsequent to the administration of all other compounds of the combination therapy.

In some embodiments, a combination of compound (A), compound (B) and optionally compound (C), or a pharmaceutically acceptable salt of the foregoing, can result in an additive effect. In some embodiments, a combination of compound (A), compound (B) and optionally compound (C), or a pharmaceutically acceptable salt of the foregoing, can result in a synergistic effect. In some embodiments, a combination of compound (A), compound (B) and optionally compound (C), or a pharmaceutically acceptable salt of the foregoing, can result in a strongly synergistic effect. In some embodiments, a combination of compound (A), compound (B) and optionally compound (C), or a pharmaceutically acceptable salt of the foregoing, is not antagonistic.

As used herein, the term "antagonistic" means that the activity of the combination of compounds is less compared to the sum of the activities of the compounds in combination when the activity of each compound is determined individually (i.e., as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compounds in the combination when the activity of each compound is determined individually.

A potential advantage of utilizing a combination of compound (A), compound (B) and optionally compound (C), or a pharmaceutically acceptable salt of the foregoing, may be a reduction in the required amount(s) of the compound(s) that is effective in treating HCV, as compared to the amount required to achieve same therapeutic result when the compound(s), is administered as monotherapy. For example, the amount of compound (A) and/or compound (B), or a pharmaceutically acceptable salt of the foregoing, in a combination described herein can be less compared to the amount of compound (A) and/or compound (B), or a pharmaceutically acceptable salt of the foregoing, needed to achieve the same viral load reduction when administered as a monotherapy. Another potential advantage of utilizing a combination of compound (A), compound (B) and optionally compound (C), or a pharmaceutically acceptable salt of the foregoing, is that the use of two or more compounds having different mechanisms of action can create a higher barrier to the development of resistant viral strains compared to the barrier when a compound is administered as monotherapy.

Additional advantages of utilizing a combination of compound (A), compound (B) and optionally compound (C), or a pharmaceutically acceptable salt of the foregoing, may include little to no cross resistance between the compounds of the combination; different routes for elimination; little to no overlapping toxicities; little to no significant effects on cytochrome P450; and/or little to no pharmacokinetic interactions between the compounds of the combination.

Selection of Suitable Subjects for Treatment

In some embodiments, potential subjects are evaluated for suitability prior to treatment. This can be part of a method and/or a use for treating the subject or for selecting a treatment for HCV infection. The objectives of the evaluation include ruling out subjects for whom the treatment may be undesirable, and selecting subjects who are most likely to respond to the treatment or those most likely to have reduced or no adverse events.

Some methods and/or uses disclosed herein can be used for subjects having HCV infection. In some embodiments, the HCV infection can be a newly-diagnosed infection. In other embodiments, the HCV infection can be a chronic hepatitis C(CHC) infection.

In some embodiments, the subject can have Type 1 HCV. In some embodiments, the subject can have Type 1a HCV. In other embodiments, the subject can have Type 1b HCV.

In some embodiments, the subject can have a HCV infection exhibiting Interleukin-28B (IL-28b) CC genotype. In other embodiments, the subject can have a HCV infection exhibiting Il-28B non-CC genotype.

Some methods and/or uses described herein can be effective to achieve a sustained virologic response (SVR) at a desired time point following the last dosing. SVR is defined as HCV RNA concentration below a lower limit of quantitation, preferably below 25 IU/mL. In some embodiments, a method and/or a use described herein can provide a SVR at 4, 5, 6, 7, 8, 9, or 10 weeks. In other embodiments, a method and/or a use described herein can provide a SVR at 12, 14, 16, 18, 20, 24, 30, 36, 48, or 52 weeks (or more). In some embodiments, a method and/or a use described herein can provide a SVR at 4 weeks. In some embodiments, a method and/or a use described herein can provide a SVR at 12 weeks.

The amino acid sequence of the nonstructural (NS)5A or NS5B proteins can affect the success of the treatment methods and/or uses described herein. By treating a plurality of subjects with different NS5A or NS5B protein sequences, those sequences can be characterized as responsive or non-responsive based on whether the subject achieves SVR at a desired time point, for example, one of the timepoints in the preceding paragraph.

In some embodiments, a method and/or a use described herein for treating a subject with a HCV can further include assessing the NS5A protein sequence of the infecting HCV of a subject, and treating the subject with any of the methods and/or uses described herein if the NS5A is responsive NS5A. In other embodiments, a method and/or a use described herein for treating a subject with a HCV can further include assessing the NS5B protein sequence of the infecting HCV of a subject, and treating the subject with any of the HCV treatments described herein if the NS5B is responsive NS5B.

In some embodiments, a method and/or a use described herein for treating a subject with a HCV treatment can further include assessing whether the subject has HCV Type 1a, and if so, treating the subject with any of the HCV treatments described herein.

In some embodiments, a method and/or a use described herein for treating a subject with a HCV can further include assessing whether the subject has HCV Type 1b, and if so, treating the subject with any of the HCV treatments described herein.

In some embodiments, a method and/or a use described herein for treating a subject with a HCV can further include assessing whether the subject has HCV with Il-28 genotype CC, and if so, treating the subject with any of the HCV treatments described herein.

In some embodiments, a method and/or a use described herein for treating a subject with a HCV can further include assessing whether the subject has HCV with 1128 non-CC genotype, and if so, treating the subject with any of the HCV treatments described herein.

In some embodiments, a method and/or a use described herein for treating a subject with a HCV can further include assessing whether the subject has HCV Type 2, and if so, treating the subject with any of the HCV treatments described herein.

In some embodiments, a method and/or a use described herein for treating a subject with a HCV can further include assessing whether the subject has HCV Type 3, and if so, treating the subject with any of the HCV treatments described herein.

In some embodiments, a method and/or a use described herein for treating a subject with a HCV can further include assessing whether the subject has CHC, and if so, treating the subject with any of the HCV treatments described herein.

In some embodiments, a method and/or a use described herein described herein may further include evaluating a subject and selecting a subject for treatment with that therapy where one or more or all of the following are true:

a. In some embodiments, the subject has genotype 1 CHC. In other embodiments, the subject has genotype 2, 3, or 4 HCV. In some embodiments, the subject has shown evidence of HCV infection (optionally for at least 6 months before treatment), as defined by any 1 of the following:

b. documented HCV serology demonstrating the presence of anti-HCV antibodies at least 6 months before screening; or c. documented presence of HCV RNA at least 6 months before treatment; or d. documented evidence of fibrosis on liver biopsy; or e. FibroSure/FibroTest >0.28 and ≤0.58 at screening (Poynard T, et al., Compar Hepatol. (2004) 3:8-19) (Note: subjects with a FibroTest score ≤0.28 may be included as long as they meet any 1 of the other CHC criteria above); or f. FibroScan™ elastography liver stiffness measurement of >5.0 and ≤10.5 (Note: subjects with a FibroScan score ≤0.5.0 may be included as long as they meet any 1 of the other CHC criteria above). (Friedrich-Rust M, et al., Gastroenterol. (2008) 134(4):960-974)

g. In some embodiments, a subject can be treatment-naïve and have not received prior treatment with any interferon, immunomodulatory agent, or DAA for HCV.

h. In some embodiments, a subject selected for treatment can have plasma HCV RNA of ≥50000 IU/mL at screening.

i. In some embodiments, a subject who are treated can have some or all of the following laboratory values:

| Laboratory Variable | Values |
|---|---|
| Hepatitis B surface antigen | Seronegative |
| Human immunodeficiency virus 1 and 2 antibodies | Seronegative |
| Absolute neutrophil count | $\geq 1000/mm^3$ |
| Albumin | $\geq 3.5$ g/dL |
| Aspartate aminotransferase | $<5 \times$ upper limit of normal (ULN) |
| Alanine aminotransferase | $<5 \times$ ULN |
| Platelet count | $\geq 140000/mm^3$ |
| Hemoglobin | $\geq 11$ g/dL for female subjects $\geq 12$ g/dL for male subjects For subjects who have baseline hemoglobin below the lower limit of normal, attention should be paid to correctable causes of anemia such as iron, folate, or B12 deficiency. |
| Total bilirubin | $<2 \times$ ULN, except in subjects with Gilbert's syndrome |
| All other hematology and clinical chemistry results | No clinically significant abnormalities or laboratory values that preclude treatment. Subjects with hemophilia may be enrolled with approval of the medical monitor. |

The methods and/or uses disclosed herein can further include selecting and treating a subject without one, a plurality, or all of the following conditions:
 a. Active alcohol abuse within 6 months before screening;
 b. Opioid replacement therapy, unless the dose has been stable for at least 3 months before screening;
 c. Uncontrolled hypertension (e.g., as determined by change in medication for reasons related to efficacy within the 3 months); and
 d. Uncontrolled diabetes mellitus (e.g., as determined by change in medication for reasons related to efficacy within 3 months or HgbA1c>7.5%).
 e. Evidence of cirrhosis, as determined by any 1 of the following:
  1. FibroSure/FibroTest score >0.58;
  2. FibroScan score >10.5 kPa;
  3. Magnetic resonance elastography of $\geq 5.98$ kPa; (Wang Y et al., AJR Am J. Roentgenol. (2011) 196(3):553-61)
  4. Liver biopsy (criteria for cirrhosis may include a scoring system compatible with bridging fibrosis with many septa or cirrhosis [e.g., Metavir F3 or F4 or Ishak $\geq 4$]); or
  5. History of ascites, hepatic encephalopathy, or esophagogastric varices.
 f. History of febrile illness within 5 days before the first treatment.
 g. Family history of prolonged QT syndrome (torsade de pointes) or sudden cardiac death; first-degree relative with myocardial infarction at premature age ($\leq 45$ years for male relative; $\leq 55$ years for female relative).
 h. 12-lead ECG demonstrating corrected QT interval (QTc)>450 milliseconds for male subjects and >480 milliseconds for female subjects at the Screening Visit. If QTc exceeds these limits, the ECG should be repeated 2 more times, and the average of the 3 QTc values used to determine the subject's eligibility.
 i. History or other clinical evidence of significant or unstable cardiac disease (e.g., prolonged QT syndrome [torsade de pointes], angina, congestive heart failure, myocardial infarction, diastolic dysfunction, significant arrhythmia, coronary heart disease, and/or clinically significant ECG abnormalities).
 j. Screening echocardiogram with left ventricular ejection fraction (LVEF) of <60%, $\geq$Stage II diastolic dysfunction, or moderate to severe valvular heart disease.
 k. Blood donation of approximately 1 pint (500 mL) or more within 56 days before first drug dose.
 l. Active malignant disease or history of malignant disease within 5 years before screening, with the exception of successfully treated basal cell carcinoma, squamous cell cancer of the skin, and carcinoma of the cervix in situ.
 m. Any other cause of significant liver disease in addition to hepatitis C, which may include but is not limited to malignancy with hepatic involvement, hepatitis B, drug-induced or alcohol-related liver disease, autoimmune hepatitis, hemochromatosis, Wilson's disease, nonalcoholic steatohepatitis, or primary biliary cirrhosis.
 n. Creatinine clearance $\leq 50$ mL/min using the Cockcroft-Gault equation (Cockcroft D. W. et al., Nephron. (1976) 16(1):31-41) at screening.
 o. Diagnosis of or suspected hepatocellular carcinoma as evidenced by screening alpha-fetoprotein $\geq 200$ ng/mL. If the alpha-fetoprotein at screening is $\geq 50$ ng/mL and <200 ng/mL, the absence of liver mass must be documented by imaging within 6 months before the first drug dose.
 p. History of organ transplant, with the exception of corneal transplants and skin grafts.
 q. A medical condition that requires frequent or prolonged use of systemic corticosteroids or immunosuppressive drugs (e.g., severe asthma; severe arthritis or autoimmune conditions; organ transplantation; or acute adrenal insufficiency); with the exception of chronic systemic corticosteroid solely for the purposes of adrenal replacement.
 r. Any condition possibly affecting drug absorption (e.g., gastrectomy or other significant gastrointestinal tract surgery, such as gastroenterostomy, small bowel resection, or active enterostomy).
 s. Glycosylated hemoglobin (HbA1C)>7.5% at screening.
 t. C-reactive protein >3 mg/dL at screening.

In some embodiments, a method and/or use described herein can further include a method of selecting a treatment for a subject having HCV, comprising evaluating whether the subject meets one or more of the specified criteria for treatment specified above, and/or whether the subject does not meet one or more of the specified exclusion criteria above, and if so, treating the subject with an effective amount of a combination of compound (A), compound (B) and optionally compound (C), or a pharmaceutically acceptable salt of the foregoing.

Some embodiments described herein relate to a method of treating a subject having HCV, that can include administering an effective amount of a combination of compound (A), compound (B) and optionally compound (C), or a pharmaceutically acceptable salt of the foregoing, wherein the subject meets one or more of the specified criteria for treatment specified above, and/or whether the subject does not meet one or more of the specified exclusion criteria above.

Some embodiments described herein relate to a method for treating HCV infection using a method and/or use described herein that can further include monitoring the subject for signs of virologic failure, and if so, discontinuing the treatment.

Virologic failure is defined as subjects with an on-treatment increase of >1 log 10 in HCV RNA levels compared to the lowest recorded on-treatment value (nadir), or subjects with confirmed on-treatment ≥LLOQ (lower limit of quantitation) HCV RNA levels after previously having ≤LLOQ HCV RNA levels on treatment, or subjects who have relapse (i.e., subjects with <LLOQ HCV RNA levels at last planned dose of treatment who develop ≥LLOQ HCV RNA levels during the Virologic Follow-up Period).

In some embodiments, a method and/or use described herein can further include monitoring the subject for seroconversion to HIV positive status, and if so, discontinuing the treatment.

In some embodiments, a method and/or use described herein can further include monitoring the subject for signs of virologic breakthrough, and if so, discontinuing the treatment.

In some embodiments, a method and/or use described herein can further include monitoring the subject for one or more of the following conditions, and discontinuing treatment if one of the following criteria is met:

the subject exhibits liver chemistry stopping criterion, specifically alanine aminotransferase level increases of at least 5× baseline, or an increase to greater than 20× of normal levels;

the subject exhibits confirmed ≥Grade 3 elevations in serum creatinine;

the subject exhibits confirmed Grade 4 elevation in creatine kinase in the absence of trauma;

the subject exhibits confirmed QT interval corrected (QTc) increased by 60 milliseconds from baseline, QTc interval >500 milliseconds, uncorrected QT interval >600 milliseconds, or QTc interval >530 milliseconds in subjects with bundle branch block (based on average QTc value of triplicate ECGs) at any time after randomization; or the subject has an echocardiogram with an absolute decrease in left ventricular ejection fraction (LVEF) of >10% from screening.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. Additionally, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

EXAMPLES

Example 1

Treatment Regime 1

The subjects are divided into 4 groups, all compounds are administered orally for 12 weeks. Virology follow-up is conducted 4 weeks to 48 weeks after the last planned dose of treatment.

| Group | Compound (A) | Compound (B) | Compound (C) |
|---|---|---|---|
| 1 | 100 mg (qd) | 60 mg (qd) | — |
| 2 | 100 mg (qd) | 60 mg (qd) | *(bid) |
| 3 | 200 mg (qd) | 60 mg (qd) | — |
| 4 | 200 mg (qd) | 60 mg (qd) | *(bid) |

*Compound (C) is administered orally, at a total daily dose of 1000 mg/day for subjects weighing <75 kg and 1200 mg/day for subjects weighing ≥75 kg.

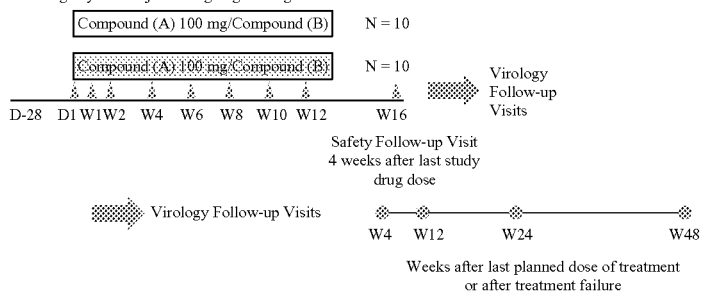

Example 2

Treatment Regime 2

The subjects were divided into 2 groups (Group 1-11 subjects and Group 2-12 subjects). The subjects were treatment-naïve genotype 1 without liver cirrhosis, and a portion of these subjects were infected with genotype 1a. All compounds were administered orally for 12 weeks via the schedule provided below. Virology follow-up were conducted 4 weeks to 48 weeks after the last planned dose of treatment.

| Group | Compound (A) | Compound (B) |
|---|---|---|
| 1 | 100 mg (qd) | 60 mg (qd) |
| 2 | 200 mg (qd) | 60 mg (qd) | qd = once daily

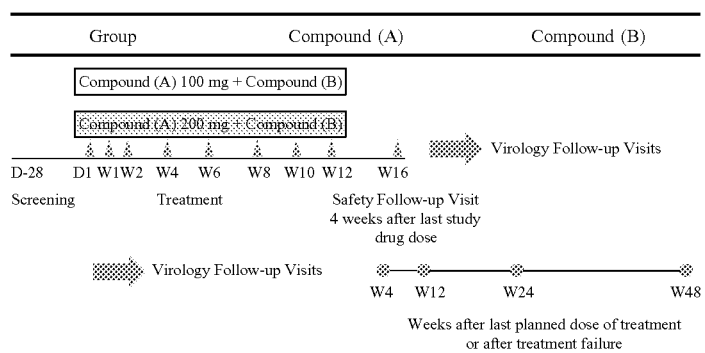

Results for Group 1:

After 4 weeks of treatment, 73 percent (8 of 11) of the subjects achieved undetectable HCV RNA (less than 25 IU/mL). Further, at 4 weeks after completion of treatment, 73% (8 of 11) of the subjects achieved undetectable HCV RNA. The 73% (8 of 11) of the subjects still achieved undetectable HCV RNA at 12 weeks after completion of treatment. Only 2 of the 11 subjects experienced viral breakthrough while receiving the combination regiment, and only 1 of 11 subjects relapsed during the follow-up visits.

Results for Group 2:

After 4 weeks of treatment, 58 percent (7 of 12) of the subjects achieved undetectable HCV RNA (less than 25 IU/mL). In addition, at 4 weeks after completion of treatment, 83% (10 of 12) of the subjects achieved undetectable HCV RNA. The 83% (10 of 12) of the subjects still achieved undetectable HCV RNA at 12 weeks after completion of treatment. Only 1 of the 12 subjects discontinued treatment due to vomiting and nausea. Of the 11 subjects who then completed the 12 weeks treatment, 10 of 11 (91%) achieved a sustained viral response at both 4 and 12 weeks after completion of treatment.

As demonstrated by the results for Groups 1 and 2, more than 73% of subjects, and as high as 91%, achieved a sustained viral response 4 weeks after completion of treatment. At 12 weeks after completion of treatment, still more than 73% of subjects, and as high as 91%, achieved a sustained viral response. By comparison only 39-50% of genotype 1 subjects achieved a sustained viral response using the current standard of care. (see Casey et al., Curr Opin Gastroenterol. (2013) 29(3):243-249; and Pearlman et al., Gastroenterol. Hepatol. (2010) 6(3 Suppl 6):1-12. Thus, the combination of compound (A) and compound (B), or a pharmaceutically acceptable salt of the foregoing, provides a significant advancement for treating HCV.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for ameliorating or treating a hepatitis C viral infection in a subject in need thereof comprising administering to the subject infected with HCV an effective amount of a combination of compound (A) and compound (B), or a pharmaceutically acceptable salt of the foregoing;

wherein:

compound (A) is

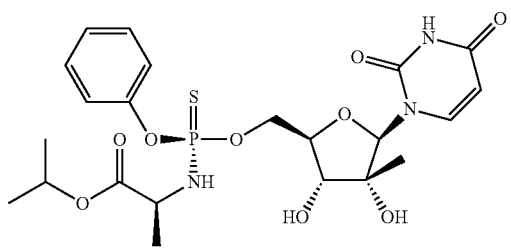 [SMILES: CC(C)OC(=O)[C@H](C)N[P@](=S)(OC[C@H]1O[C@@H](n2ccc(=O)[nH]c2=O)[C@](C)(O)[C@@H]1O)Oc1ccccc1]

and administered in a dosage amount in the range of 50 mg to 300 mg; and compound (B) is

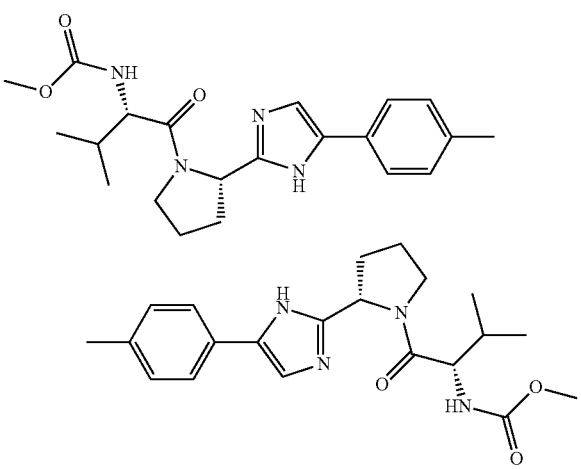

(daclatasvir) and administered in a dosage amount in the range of about 40 mg to about 80 mg.

2. The method of claim 1, wherein compound (A) is administered in a dosage amount in the range of 100 mg to 200 mg.

3. The method of claim 1, wherein compound (A) is in an amount of 100 mg.

4. The method of claim 1, wherein compound (A) is in an amount of 200 mg.

5. The method of claim 1, wherein compound (A) is administered once daily.

6. The method of claim 1, wherein compound (A) is administered orally.

7. The method of claim 1, wherein compound (B) is administered in a dosage amount in the range of 50 mg to 70 mg.

8. The method of claim 1, wherein compound (B) is in an amount of 60 mg.

9. The method of claim 1, wherein compound (B) is administered once daily.

10. The method of claim 1, wherein compound (B) is administered orally.

11. The method of claim 1, wherein the combination is provided for less than 24 weeks.

12. The method of claim 1, wherein the hepatitis C virus is a genotype selected from 1, 2, 3, 4, 5 and 6.

13. The method of claim 12, wherein the hepatitis C virus is a genotype 1.

14. The method of claim 13, wherein the genotype 1 is genotype 1a.

15. The method of claim 12, wherein the hepatitis C virus is a genotype 2.

16. The method of claim 12, wherein the hepatitis C virus is a genotype 3.

17. The method of claim 1, wherein the subject is a naïve subject.

18. The method of claim 1, wherein the subject has liver cirrhosis.

19. The method of claim 1, wherein the hepatitis C viral infection is a chronic HCV infection.

20. The method of claim 1, wherein the method further comprises selecting a subject for treatment based on one or more criteria selected from responsive NS5A amino acid sequence, responsive NS5B amino acid sequence, assessment of infection with HCV type 1a, assessment of infection with HCV type 1b, assessment of infection with Il-28B CC genotype, assessment of infection with Il-28B non-CC genotype, assessment of infection with HCV type 2, assessment of infection with HCV type 3 and assessment of CHC.

21. The method of claim 1, wherein the combination further comprises compound (C), or a pharmaceutically acceptable salt thereof, wherein compound (C) is

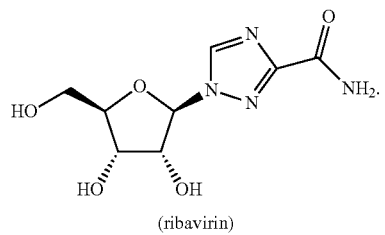 [SMILES: NC(=O)c1ncn([C@@H]2O[C@H](CO)[C@@H](O)[C@H]2O)n1]

(ribavirin)

22. The method of claim 21, wherein compound (C) is administered twice daily.

23. The method of claim 21, wherein the total daily dose of compound (C) is in an amount in the range of about 800 mg to about 1400 mg.

* * * * *